(12) United States Patent
Stewart et al.

(10) Patent No.: US 7,607,357 B2
(45) Date of Patent: Oct. 27, 2009

(54) AUTOMATED TEST SYSTEMS CONFIGURED TO EVALUATE PROPERTIES OF PACKAGING FILM AND RELATED METHODS

(75) Inventors: Gary Stewart, Raleigh, NC (US); William Arthur Schlieper, II, Cary, NC (US)

(73) Assignee: Enepay Corporation, Raleigh, NC (US)

( * ) Notice: Subject to any disclaimer, the term of this patent is extended or adjusted under 35 U.S.C. 154(b) by 216 days.

(21) Appl. No.: 11/675,165

(22) Filed: Feb. 15, 2007

(65) Prior Publication Data
US 2007/0204701 A1    Sep. 6, 2007

Related U.S. Application Data

(60) Provisional application No. 60/778,293, filed on Mar. 2, 2006.

(51) Int. Cl.
*G01N 3/08* (2006.01)
(52) U.S. Cl. ........................................................ 73/827
(58) Field of Classification Search .................... 73/827
See application file for complete search history.

(56) References Cited

U.S. PATENT DOCUMENTS

| | | | | |
|---|---|---|---|---|
| 2,473,517 A | | 6/1949 | Freedman | 73/150 |
| 3,396,578 A | * | 8/1968 | Skundberg | 73/150 A |
| 3,412,606 A | * | 11/1968 | Cooper et al. | 374/15 |
| 3,580,065 A | * | 5/1971 | Strittmater et al. | 73/150 R |
| 3,678,740 A | * | 7/1972 | Schmid et al. | 73/794 |
| 3,777,452 A | * | 12/1973 | Koenders | 53/206 |
| 3,788,135 A | * | 1/1974 | Hammond, Jr. | 374/15 |
| 3,925,139 A | | 12/1975 | Simmons | 156/358 |
| 3,937,071 A | * | 2/1976 | Slota et al. | 73/809 |
| 4,548,141 A | * | 10/1985 | Freermann | 112/113 |
| 4,637,252 A | * | 1/1987 | Rhee et al. | 73/150 A |
| 4,716,766 A | * | 1/1988 | Baureis | 73/827 |
| 4,795,413 A | | 1/1989 | Johnson et al. | 493/309 |
| 5,155,956 A | | 10/1992 | Norment et al. | 52/217 |
| 5,205,650 A | | 4/1993 | Rasmussen | 383/107 |
| 5,331,858 A | | 7/1994 | Theller | |
| 5,404,751 A | * | 4/1995 | Beran et al. | 73/150 A |
| 5,439,539 A | | 8/1995 | McLean | 156/64 |
| 5,462,807 A | * | 10/1995 | Halle et al. | 428/500 |
| 5,692,606 A | | 12/1997 | Elmalch | 206/278 |
| 5,847,284 A | | 12/1998 | Theller | |
| 5,868,901 A | | 2/1999 | Smith | 156/582 |
| 5,972,396 A | | 10/1999 | Jurgovan et al. | 426/106 |

(Continued)

OTHER PUBLICATIONS

Enepay Corporation "Magma Hot Tack and Heat Seal Test System; Installation, Operation and Maintenance" Version 1.00 1-21 (Version 1, Apr., 2005).

(Continued)

*Primary Examiner*—Harshad Patel
*Assistant Examiner*—Octavia Davis
(74) *Attorney, Agent, or Firm*—Myers, Bigel, Sibley & Sajovec, P.A.

(57) ABSTRACT

The testing systems can incorporate one or more of: (a) side-insertion peel clamps for faster operator loading of film specimens; (b) integral calibration platforms in the peel grip assemblies for convenient calibration of the peel force transducers; and (c) a positioning assembly to hold in place aged specimens in preparation for peeling tests.

14 Claims, 8 Drawing Sheets

U.S. PATENT DOCUMENTS

| | | | |
|---|---|---|---|
| 6,230,781 B1 | 5/2001 | Smith | 156/582 |
| 6,344,258 B1 * | 2/2002 | Rasmussen | 428/174 |
| 6,478,264 B1 | 11/2002 | Nelson et al. | 248/65 |
| 6,609,055 B2 | 8/2003 | Stanley | 701/45 |
| 6,763,728 B1 * | 7/2004 | Albrecht | 73/838 |
| 6,832,525 B2 * | 12/2004 | Nelson et al. | 73/827 |
| 6,952,959 B2 * | 10/2005 | Hishinuma | 73/159 |
| 7,179,334 B2 | 2/2007 | Montano et al. | 156/247 |

OTHER PUBLICATIONS

International Search Report and Written Opinion for International Application PCT/US2007/04411, International Filing date Feb. 20, 2007, Date of Mailing Mar. 11, 2008.

Dolen et al., Adhesive Bond Testing Apparatus, Defensive Publication T916,005, Published Nov. 27, 1973, United States Patent Office.

* cited by examiner

AUTOMATED TEST SYSTEMS CONFIGURED TO EVALUATE PROPERTIES OF PACKAGING FILM AND RELATED METHODS

RELATED APPLICATIONS

This application claims the benefit of priority to U.S. Provisional Application Ser. No. 60/778,293, filed Mar. 2, 2006, the contents of which are hereby incorporated by reference as if recited in full herein.

FIELD OF THE INVENTION

The present invention relates to test equipment used to evaluate properties of flexible packaging materials, and may particularly suitable to evaluate heat-sealable films.

BACKGROUND

Food and other products are increasingly manufactured, distributed and utilized in flexible packaging that employ a variety of plastic films. The flexible packaging is typically in the form of a pouch or bag, in which one or more sides are sealed together, typically heat-sealed together, to contain the product within. To facilitate proper sealing, the packaging film should have acceptable properties to allow for one or more of: (a) high-speed production; (b) inhibition of product loss during distribution; and/or (c) ease of opening by the end-user. Proper sealing characteristics arise from an appropriate combination of seal pressure, seal temperature and seal duration during the manufacturing process. To find a suitable (or even optimal) combination, three types of laboratory tests can be performed: a Hot Tack Test, a Heat Seal Test, and an Aged Seal Test. In these tests, several samples (e.g., at least three samples) are typically evaluated of each film batch or type at a given test condition to facilitate reliable and/or statistically accurate testing data.

Known commercially available systems that perform some or all of the basic Hot Tack, Heat Seal and Aged Seal tests include: (a) the Hottack 3000, manufactured by J&B Material Tester, Belgium; (b) the HTH2 Hot Tack Heat Sealer, manufactured by Dynisco Instruments, Franklin, Mass.; (c) the SL 10 Hot Tack Tester, manufactured by Lako Tool, Perrysburg, Ohio, and (d) the Magma Heat Seal & Hot Tack Tester, manufactured by Enepay Corporation, Raleigh, NC. U.S. Pat. Nos. 5,331,858 and 5,847,284 to H. Theller also describe packaging film testing devices; the contents of these patents are hereby incorporated by reference as if recited in full herein.

SUMMARY OF EMBODIMENTS OF THE INVENTION

Embodiments of the present invention provide improved automated testing systems that can automatically perform one or more of the Hot Tack, Heat Seal and/or Aged Seal tests on a plurality of different samples and electronically obtain testing evaluation data of each of the samples. The testing of the different specimens can be run serially or substantially simultaneously, although typically the latter is conducted.

In some embodiments, the testing systems can perform automated Hot Tack, Heat Seal and Aged Seal tests on at least three film samples substantially simultaneously.

The testing systems can incorporate one or more of: (a) side-insertion peel clamps for faster operator loading of film specimens; (b) integral calibration platforms in the peel grip assemblies for convenient calibration of the peel force transducers; and (c) a positioning assembly to hold in place aged specimens in preparation for peeling tests.

Some embodiments are directed to automated or semi-automated packaging film testing systems configured to perform at least one of a hot tack test, a heat seal test and an aged seal test. The systems can include at least one specimen test station, the at least one test station comprising cooperating and upper and lower side-insertion peel clamps configured to allow a film specimen to be inserted therein to releasably hold the film specimen during at least one of an automated: (a) hot tack test, (b) heat seal test and (c) aged seal test, wherein at least one of the upper and lower peel clamps is automatically translatable during the at least one automated testing cycle.

Some embodiments are directed to automated or semi-automated packaging film testing devices configured to perform at least one of a hot tack test, a heat seal test and an aged seal test of a film test specimen. The devices include: at least one specimen test station, each at least one specimen test station comprising an integrated force transducer calibration platform that resides above a peel force transducer to be in communication with the peel force transducer. The integrated force transducer calibration platform is configured to allow calibrated weights to be placed thereon to allow external calibration of the peel force transducer while the peel force transducer remains in position in the device. Some embodiments are directed to automated or semi-automated packaging film testing devices that include: (a) a plurality of side-by-side test stations, each test station comprising cooperating upper and lower peel clamps configured to releasably hold a film specimen and a respective upper and lower positioning assembly in communication with the upper and lower peel clamps; and (b) a controller configured to programmatically direct the test stations to selectively carry out one of a hot tack test, a heat seal test and an aged seal test, wherein the controller is configured to direct at least one of the upper and lower positioning assemblies to automatically move so that the upper and lower clamps are positioned at a predetermined aged-seal test start location to accept an aged-seal test specimen, and wherein the positioning assembly aged-seal test start location is different than the start location of the hot tack and heat seal tests.

Other embodiments are directed to methods of evaluating packaging film. The methods include: (a) programmatically directing movement of peel clamps in a plurality of side by side testing stations of a packaging film testing system to automatically perform at least one of a hot tack test, a heat seal test and an aged seal test on respective film specimens; (b) electronically measuring peel forces associated with the directing step; and (c) electronically automatically providing test results based on the measured forces to a user.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EMBODIMENTS OF THE INVENTION

Figure 1:
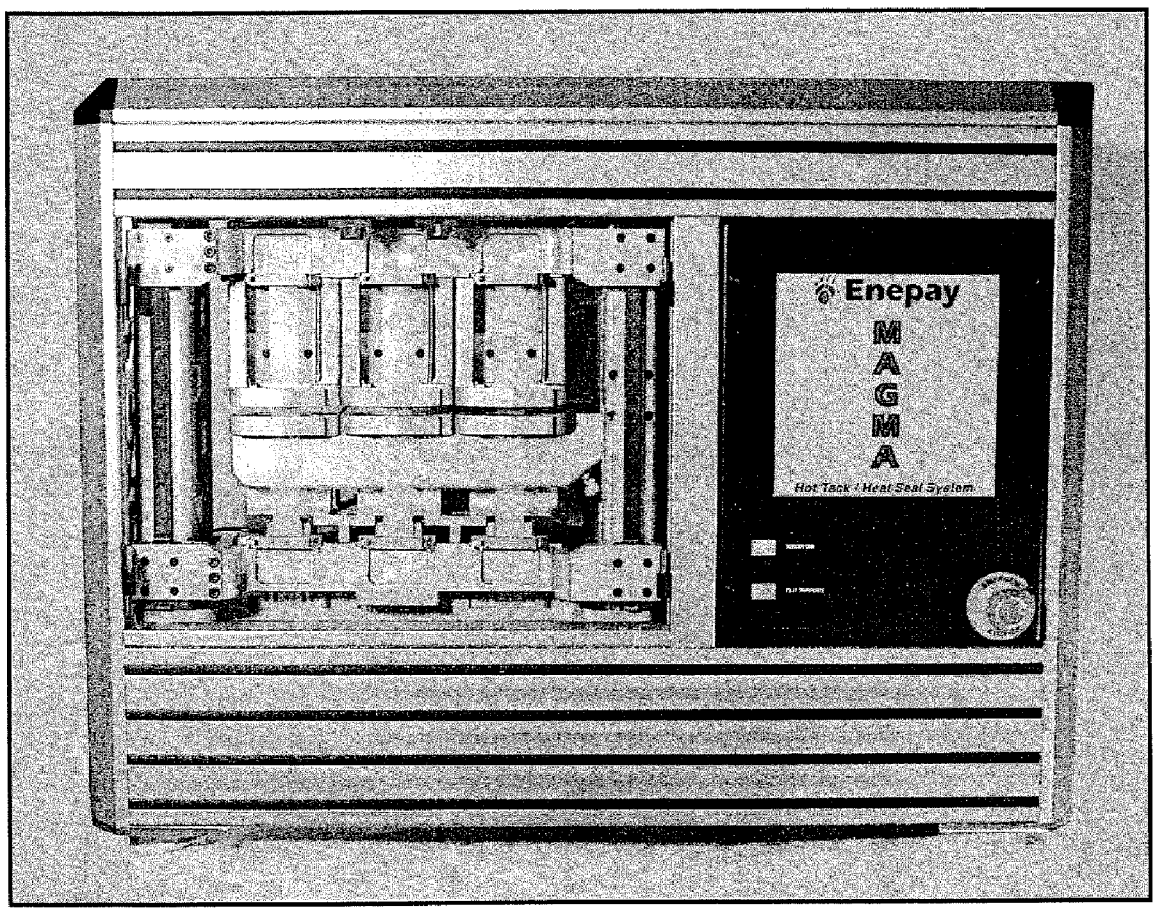
FIG. 1 is a digital photograph of a front view of an automated system with a plurality of testing stations according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. In the figures, the below reference numbers refer to the defined component(s). The description is based on a three-bay tester (three testing stations), however, lesser or greater numbers of testing stations can be used. Herein, the following reference numbers are used to identify specific components.

10—Upper positioning assembly
12—Lower positioning assembly
14—Positioning clamp and latch (qty 6)
16—Guide rail (qty 2)
18—Peel grip assembly (qty 3)
20—Upper side-insertion peel clamp (qty 3)
22—Lower side-insertion peel clamp (qty 3)
24—Peel motion arm
26—Upper seal jaws (qty 3)
28—Lower seal jaws (qty 3)
30—Specimens (qty 3)
32—Reaction frame side (qty 2)
34—Reaction frame top
36—Reaction frame bottom
38—Peel grip assembly column (set of two per peel grip assembly); only one set shown
40—Peel force transducer (qty 3); only one shown
42—Calibration platform (qty 3)
44—Calibration weight; (typically not provided as part of the system)
46—Folding assembly The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The packaging film that can be evaluated using methods and devices contemplated by the instant invention can be a single ply or multiple ply material. The film can be laminated. The film can be elastomeric. The film can comprise a polymer, copolymer or blend or derivative thereof. The film can also comprise foil or other materials. The test samples are typically provided as a single elongate strip of the film. The test samples can be between 8-16 inches long, typically at least about 10 inches long, with a width between about 1-2 inches, typically between about 1-1.6 inches. The test samples should be prepared in sufficient quantity to run them through all desired testing temperatures. The test samples should be oriented with the seal surface facing in the same direction (typically facing the operator) for insertion/loading and/or testing in the system.

The term "automated" means that the operations are carried out without requiring operator assistance or input. The term "semi-automated" means that the device is programmatically and electronically configured to perform the operations substantially without manual labor but may accept user input to select functions load and unload film and the like.

The three basic tests that can be automatically or semi-automatically performed are generally described below. Although described as capable of performing all three, the inventions are not limited thereto as systems may optionally be configured to carry out only one, two or all three of the tests and may also perform other tests of interests.

Hot Tack Test

The Hot Tack Test measures the strength of a heat seal at a short time interval after a seal is made and before it has cooled down to its peak strength. This is an indicator of the seal's ability to withstand the stress of the product filling operation during manufacturing, when the seal may not be (and typically is not) fully cooled and at full strength. This test can be performed by:

a) folding a strip of sample film back on itself to form two layers of film, b) sealing those two layers together (simulating a pouch or bag seal) by applying pressure between two seal dies under controlled conditions of pressure, temperature and duration, c) releasing the die pressure, d) quickly extracting the sealed sample from the dies, then peeling the sealed section apart while measuring the peel force to do so, e) recording the pulling forces at specific time intervals from extraction from the dies, which are typically at between about 0.25 second to about 0.50 second intervals, then f) repeating the above tests with different samples at specific temperature steps in order to create a curve of the film's hot tack strength vs. temperature.

Heat Seal Test

The Heat Seal Test measures the strength of a heat seal after it has cooled to ambient temperature and has reached stability. This is an indicator of the seal's ability to withstand the packaging stresses found in handling and distribution. This test is done by:

a) folding a strip of sample film back on itself to form two layers of film, b) sealing those two layers together (simulating a pouch or bag seal) by applying pressure between two seal dies under controlled conditions of pressure, temperature and duration, c) releasing the die pressure, d) extracting the sealed sample from the dies, e) cooling the recently formed seal to ambient temperature, typically by directing cooling air over the seal, f) peeling apart the sealed section while continuously measuring the force to do so, g) recording the peak force measured during the peel operation, and h) repeating the above tests with different samples at specific temperature steps in order to create a curve of the film's peak strength vs temperature.

Aged Seal Test

The Aged Seal Test measures the strength of a heat seal after a prolonged time period (thus the term "aged"). The time period is typically days, weeks, or even months. This is an indicator of the seal's ability to maintain strength over long periods of time and thus preserve product freshness. The Aged Seal Test can be considered a variation of the Heat Seal Test, with the difference being a longer time period between sealing and peeling apart the specimen seal. This test can be done by:

a) folding a strip of sample film back on itself to form two layers of film, b) sealing those two layers together (simulating a pouch or bag seal) by applying pressure between two seal dies under controlled conditions of pressure, temperature and duration, c) releasing the die pressure, d) extracting the sealed sample film from the dies, e) storing the sealed sample film for the required extended time, f) repeating the above sealing operations with different samples at specific temperature steps, g) for each aged sample, peeling apart the sealed section while continuously measuring the force to do so, h) for each aged sample, recording the peak force measured during the peeling operation, and i) for the entire set of aged samples, creating a curve of the film's peak strength vs. temperature.

Reaction Frame

Figure 2:
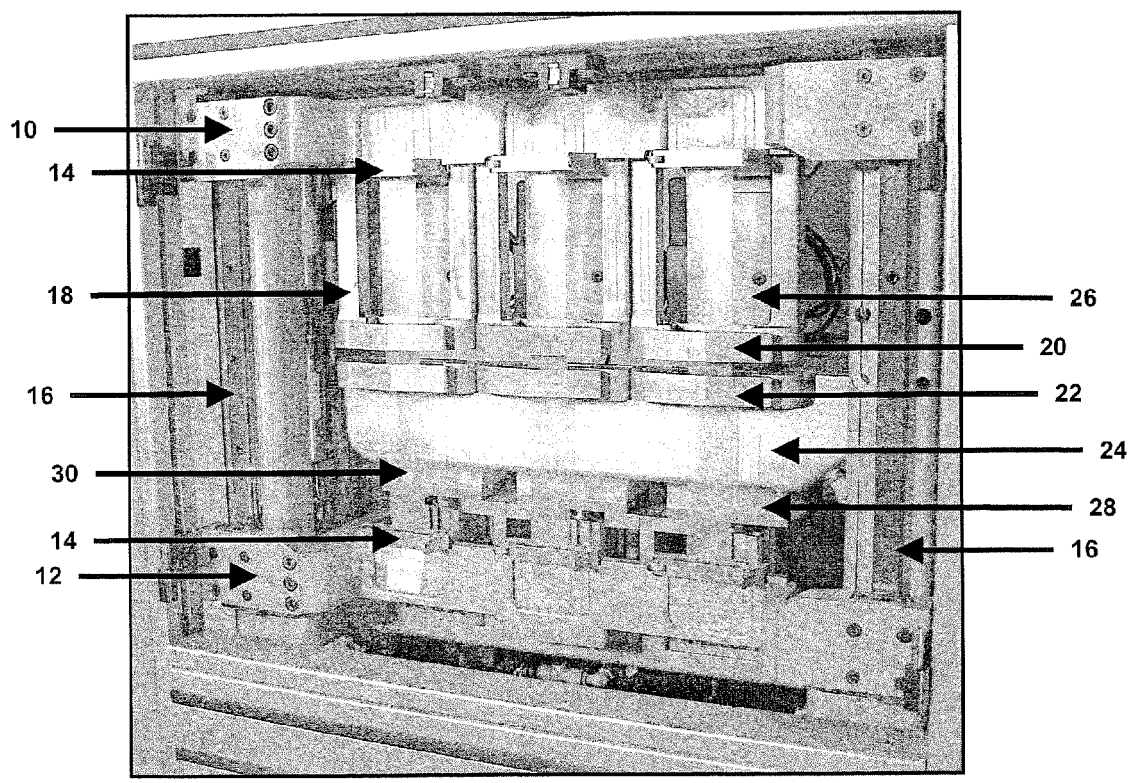
FIG. 2 is a digital photograph of a side perspective view of the system shown in FIG. 1 illustrating various specimen-handling devices.
Figure 3:
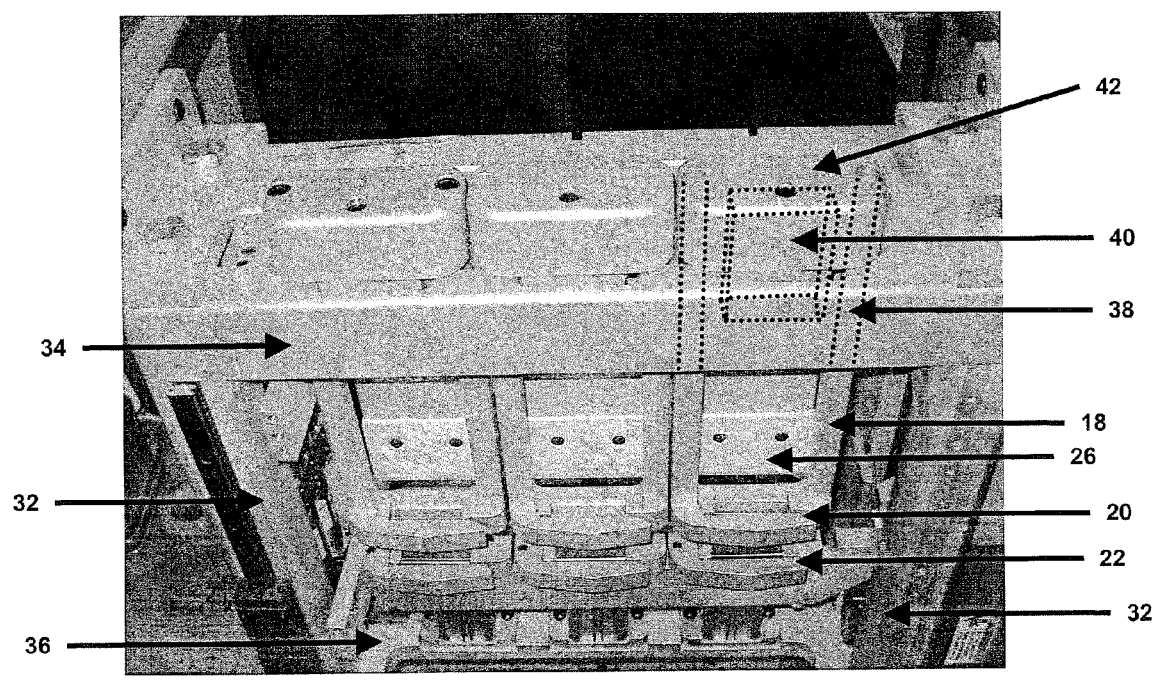
FIG. 3 is a digital photograph of a top perspective view of the device shown in FIG. 1 illustrating peel grip assemblies mounted in the frame, with the broken lines showing the "hidden" peel force transducers and the "hidden" peel grip assembly columns. The positioning assemblies are removed for clarity.

As shown in FIGS. 2 and 3, the reaction frame sides 32, reaction frame top 34 and reaction frame bottom 36, form the platform to which the other mechanical components are mounted.

Positioning Assemblies

Referring to FIGS. 2-5, upper positioning assembly 10 and lower positioning assembly 12 move vertically on guide rails 16 under control of pneumatic cylinders. Each assembly has three positioning clamps and latches 14 which hold the ends of three film specimens 30. Operating in unison with folding assembly 46, the upper and lower positioning assemblies 10, 12 move the film into various positions during the test cycle.

The upper and lower positioning assemblies 10, 12 are configured to reside in (or travel to) one of three positions, depending on the test step. The first position is the "load" position where they are farthest apart; this is the location used to load specimens in preparation for some of the testing. The next position is the "sealing" position where they are closest together; this is where the specimens 30 have been pulled through the seal jaws and are being sealed. Finally, the third position in the test sequence is the "peel test preparation" location; this is where upper and lower positioning assemblies 10, 12 are approximately at mid-position after having extracted the specimens 30, either in preparation for the peeling test or waiting for specimen removal in the case of aged seal tests.

Peel-Grip Assemblies

Figure 4:
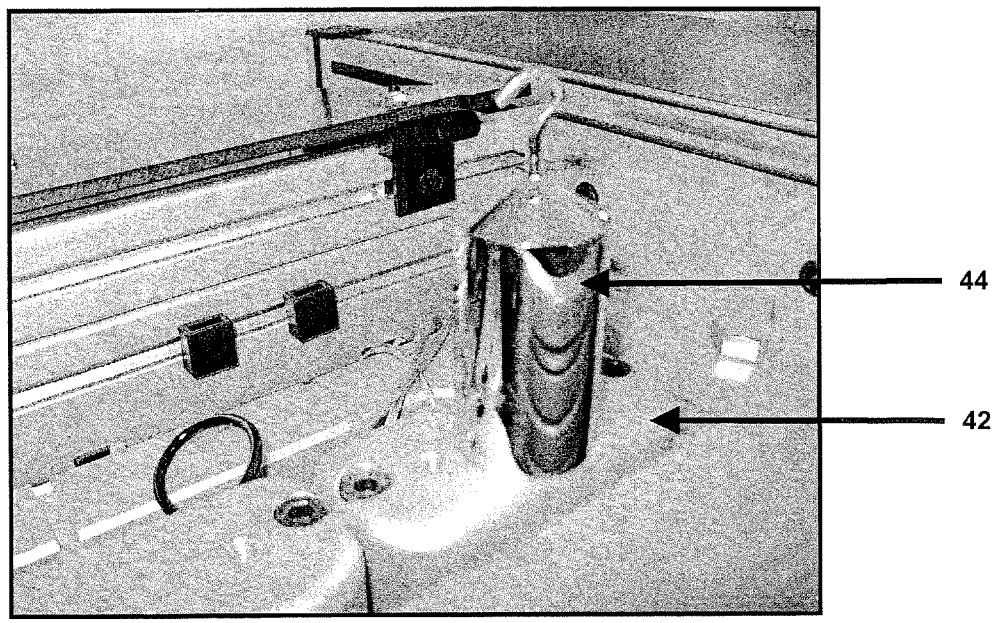
FIG. 4 is a digital photograph of the system shown in FIG. 1 illustrating a calibration platform being calibrated with a calibration weight according to embodiments of the present invention.
Figure 5:
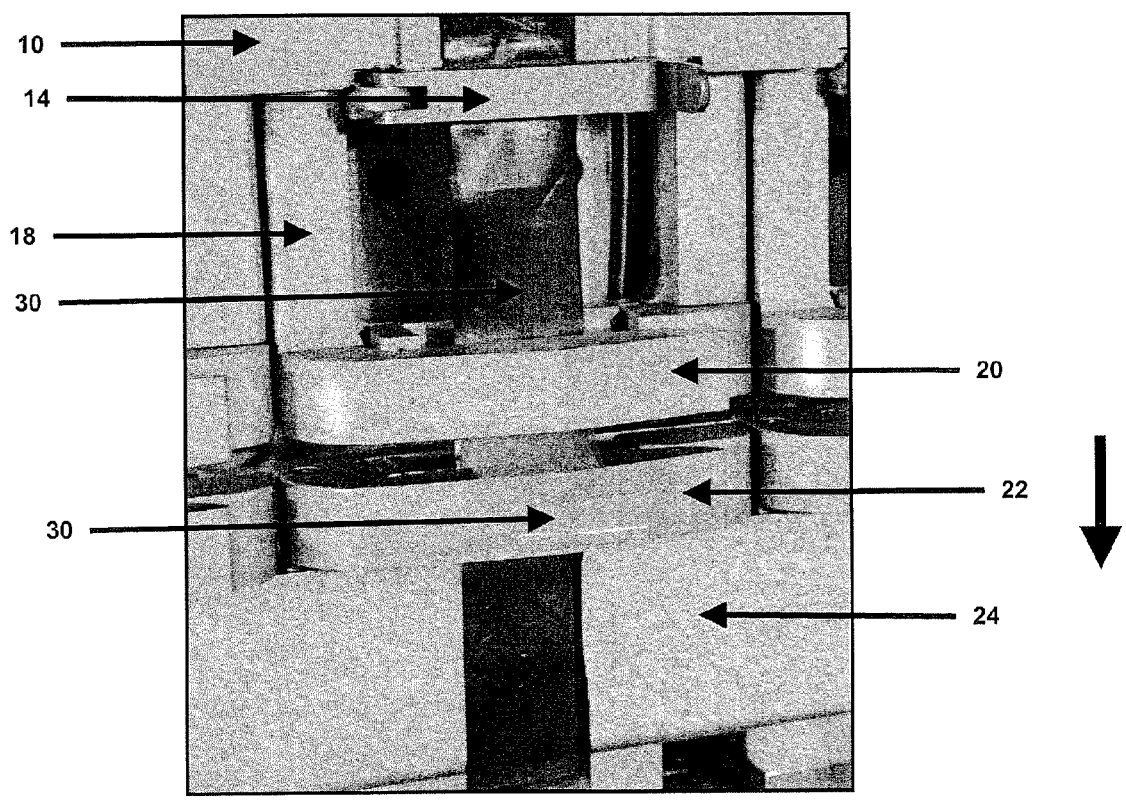
FIG. 5 is a digital photograph of an enlarged view of a portion of the system shown in FIG. 1 that shows the upper positioning assembly holding an aged specimen in preparation to run an aged seal test according to embodiments of the present invention.

Referring to FIGS. 3-5, the (three) peel grip assemblies 18 provide several functions. First, their upper side-insertion peel clamps 20 allow the film specimen 30 to be loaded into the system by simply sliding in from the side (where side entry sliding peel clamps are used), then to be clamped at either end by the positioning assemblies 10, 12. Second, they grip the film specimen 30 for peel testing by applying pressure to the film with the upper side-insertion peel clamps 20. Third, they measure the peel force exerted on the specimen 30 as the seal is peeled apart with their peel force transducers 40.

Side-Insertion Peel Clamps

Some embodiments of the invention incorporate side-insertion peel clamps for fast operator loading of film samples. The operator simply slides film samples into the open side of the peel clamps. The side-insertion peel clamps do not require latches, doors, clamps or other devices to hold film samples during the peeling operation.

The side-insertion peel clamps eliminates the need for latches, doors or other devices found in front-insertion grip assemblies. Not having to operate doors and latches can increase the speed of loading specimens into the system. Also, not having to operate doors and latches eliminates the risk of faulty data from grip slippage as a result of the operator not adequately latching the front doors. Finally, the side-insertion peel clamps can be configured to eliminate a number of moving parts and therefore increase machine reliability.

As shown in FIGS. 1, 2, 3 and 5, embodiments of invention can use the side-insertion peel clamps 20 that are rigid members and may comprise solid metal. The clamps 20 can be a unitary body with a closed side and an open side that provides for insertion of the specimen 30 from the right. Once the film is threaded or slid into position through the open gap space inside the clamp, a pincher member can automatically activate to secure the film between the inside outer leg of the clamp and the pincher member.

Alternative embodiments can:

a) provide a releasable attachment means (such as bolting, bayonet fitting, or other attachment means) on the closed end of the clamps 20 for removing the entire member or the cantilevered section for servicing or replacement;

b) reverse the orientation to allow insertion from the left side; and/or c) employ a different (automatic) releasable clamp/film attachment mechanism that cooperates with the clamp to reliably secure the film during testing.

Peel Motion Arm With Side-Insertion Peel Clamps

Referring to FIGS. 2-5, the peel motion arm 24 provides the downward peeling motion for the peel testing of the sealed specimens 30. It is mounted to three lower side-insertion peel clamps 22. The lower side-insertion peel clamps 22 can operate identically as the upper side-insertion peel clamps 20 and have the same alternative embodiments.

The peel motion arm 24 can be driven by a lead screw at a user- or test-selected speed. In some embodiments, the speed may be selected by the operator through the software at the beginning of the test. Because the lower side-insertion peel clamps 22 are mounted to this common peel motion arm 24, all three film specimens 30 can be peel-tested at precisely the same speed. Other drive systems may also be employed.

Integrated Force Transducer Calibration Platforms

As shown in FIGS. 3 and 4, some embodiments of the invention utilize integrated force transducer calibration platforms as part of the peel grip assemblies and their associated peel force transducers. Using dead weights, these platforms allow accurate and easy "in-machine" calibration of the peel force transducers because no removal of the force transducers is needed.

Each peel grip assembly 18 has two peel grip assembly columns 38 which pass freely through openings in reaction frame top 34 and which attach to calibration platform 42. Calibration platform 42 attaches to the top of peel force transducer 40, the bottom of which is affixed to the top surface of reaction frame top 34. In this way a direct, shunt-free load path is created between the peel force transducer 40 and the upper side-insertion peel clamp 20 so that accurate forces can be measured as the specimen 30 is peeled apart.

Because the calibration platforms 42 are directly attached to the peel force transducers 40 they can be used as convenient and accurate locations to place calibration weights for periodic calibration of the peel force transducers 40. As shown, the calibration platform 42 is hollow and encapsulates the peel force transducer 40.

Alternative embodiments can:

a) utilize a differently shaped platform to attach to the two peel grip assembly columns 38 and to the peel force transducers 40.

b) incorporate markings or visual indicia on the top surface of calibration platform 42 to aid in placing calibration weights in the correct location for even load distribution during calibration.

In summary, the integrated calibration platforms allow calibrated dead weights to be directly placed on top of the peel grip assemblies and their associated force transducers to perform calibrations, without having to remove the force transducers from the machine. Eliminating the requirement to remove, then reinstall, the peel force transducers can greatly reduce the time to perform calibrations and can also reduce the risk of damaging the (sensitive) transducers.

Use of Positioning Assembly for Aged Seal Tests

Some embodiments of the invention include the use of a positioning assembly to hold in place aged-specimens in preparation for peeling tests. The positioning assembly allows the operator to accurately locate and hold the sealed section of an aged sample between the upper and lower side-insertion peel clamps. FIG. 5 illustrates an exemplary "aged-specimen" test position whereby the lower side-insertion peel clamp component 22 is configured to start in this position, which allows an operator to insert the film and latch to the door 14, then the peel motion arm 22 and the peel clamp 22 translate down as indicated by the arrow, to test the seal. The peel clamp 20 may be stationary during the aged seal testing operation.

In some past designs, the seal of an aged specimen is manually placed between the upper and lower peel clamps, and relies on the specimen's sealed section to loosely hold the specimen in place between the two peel clamps. This often results in misalignments and data scatter. The advantage of using the automated, "start" position-smart positioning assembly is that it can accurately locate and hold the aged sample, which can reduce misalignments and data scatter.

Folding Assembly

Folding assembly 46 has three tines that "hook" the three film specimens 30 and pull them back between the upper seal jaws 26 and lower seal jaws in preparation for the sealing operation. It moves in two axes in a horizontal plane. During the test the folding assembly 46 first moves laterally to one side, then moves forward between the upper and lower side-insertion peel clamps 20, 22 and past the vertical plane defined by the three specimens 30. It then moves laterally in the opposite direction to bring the three tines in front of the three film specimens 30. At the point in the test when the specimens 30 are to be sealed, folding assembly 46 moves toward the rear at the same time as upper and lower positioning assemblies 10, 12 move together. In this way the specimens 30 are pulled through (essentially "folded" back on itself, thus the name of the assembly) the upper and lower seal jaws 26, 28.

Seal Jaws

The upper and lower seal jaws 26, 28 heat to the sealing test temperature set in the test parameters. The three upper seal jaws 26 are each attached to seal force transducers (different from the peel force transducers 40), which are in turn mounted to the reaction frame top 34. The lower seal jaws 28 are affixed to three pneumatic cylinders, which move upward in unison at a controlled pressure to seal against the upper seal jaws. The seal pressure is applied for the specified dwell time and then released.

Software and Controls

General

The test sequence is automated from the time that the operator initiates the test to the time that the test is complete and its results are displayed. Through a graphical user interface, test profiles can be created and saved, engineering units selected, default test directory paths set, tests initiated, observations entered during testing, data tabulated and graphed for each group of three specimens, data saved, data exported, data recalled and displayed, transducers calibrated, and many other functions performed.

Figure 6:
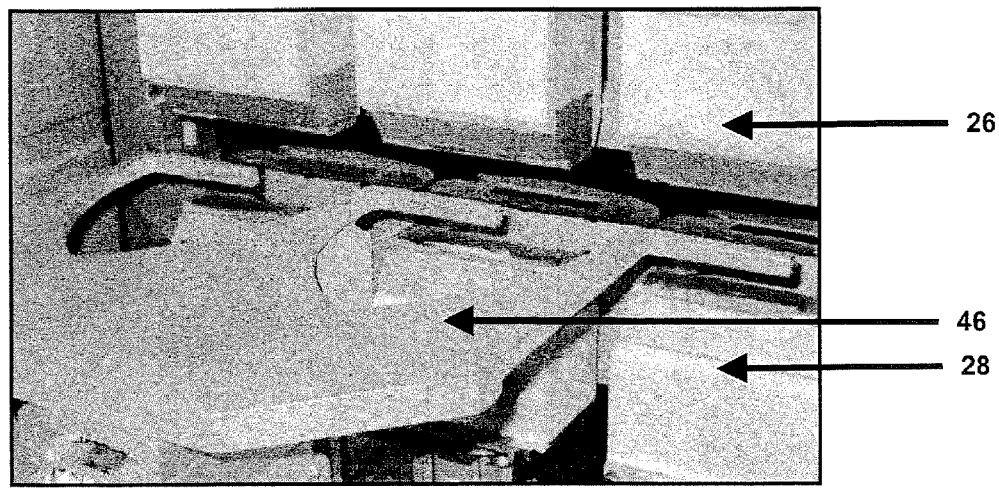
FIG. 6 is a digital photograph of a rear view of the system shown in FIG. 1 illustrating the folding assembly as seen from the rear of the system.
Figure 7:
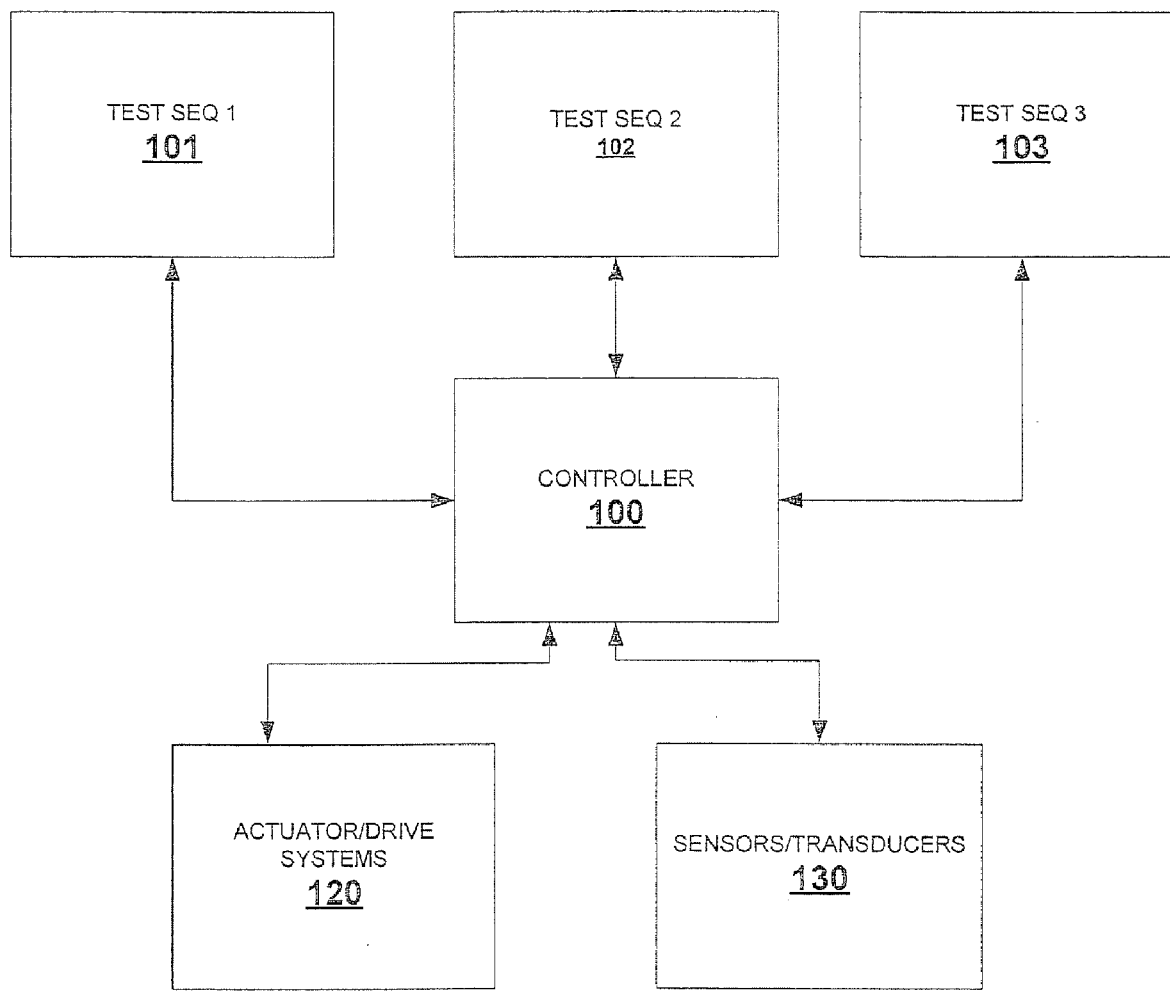
FIG. 7 is a schematic of a circuit that can be used to programmatically direct the automated operation of the system according to embodiments of the invention.

FIG. 6 is a schematic illustration of a circuit for controlling automated operation of the system. As shown, a controller 100 selects one of three pre-programmed sequences 101, 102, 103, depending on the test(s) desired. Each sequence can be in a common computer module or in a separate module. The controller 100 directs the operation of the drive system and/or actuators 120 that carry out the automated movements. The controller 100 communicates with various sensors 130 (transducers and the like) to apply the proper force, temperature, speed and the like. Data can be transferred back to the controller. Test data results can be calculated and provided to a user on a display or via other desired output.

Use of Positioning Assembly for Aged Seal Tests

The invention includes programmatic (software) control of the upper positioning assembly 10 to move it to the "peel test preparation" "start" position before performing a peel test on an aged seal specimen. Using the upper positioning assembly 10 in such a way can result in more accurately aligned specimens in the upper and/or lower seal jaws 26, 28 and greatly reduce data scatter, as compared to allowing a specimen's sealed section to loosely and unreliably hold the specimen in place between the two peel clamps.

Exemplary Test Sequences

Test Type 1

The invention may operate in the following sequence for Hot Tack Tests, Heat Seal Tests, and for the initial sealing operation in Aged Seal Tests:

a) Operator inputs test parameters.

b) Operator loads specimens 30 by inserting them into the upper and lower side-insertion peel clamps 20, 22, then by clamping their upper and lower ends with the positioning clamps and latches 14 in the upper and lower positioning assembly 10, 12.

c) Operator starts automated test.

d) Upper and lower seal jaws 26, 28 heat up to the specified temperature.

e) Folding assembly 46 moves forward to front of specimens 30.

f) Simultaneously, upper and lower positioning assemblies 10, 12 move from "load" position to "sealing" position, and folding assembly 46 moves rearward, thereby pulling specimens 30 between upper and lower seal jaws 26, 28.

g) Lower seal jaws 28 move up to the upper seal jaws 26 at the specified pressure and for the specified dwell time, thereby sealing specimens 30.

h) Folding assembly 46 moves laterally to release the specimens 30.

i) Lower seal jaws 28 retract and release the specimens 30.

j) Upper and lower positioning assemblies 10, 12 move to the "peel test preparation" location.

Either (in the case of sealing specimens 30 for Aged Seal testing):

k) Operator removes specimens 30 and set them aside for aged seal testing later.

l) Test is over.

m) Test can be repeated at new temperature.

Or (in the case of a Hot Tack or Heat Seal test):

k) Upper and lower peel clamps 20, 22 activate to clamp the specimens 30.

l) Peel motion arm 24 performs the peeling test by moving down at the specified test rate.

m) Force data is simultaneously collected with the peel force transducers 40.

n) Upon completion of peeling test, data is displayed and stored.

o) Operator removes specimens 30.

p) All assemblies are moved to initial positions.

q) Test can be repeated at new temperature.

Test Type 2

The device can operate in the following sequence for the final peeling test in Aged Seal Tests:

a) Operator inputs test selection/commands via the user interface, causing the upper and lower positioning assemblies 10, 12 to move to the "peel test preparation" position.

b) Operator loads specimens 30 by clamping their upper ends with the positioning clamp and latch 14 in the upper positioning assembly 10, while keeping the sealed section located between the upper and lower side-insertion peel clamps 20, 22. Clamping the lower ends of specimens 30 is not necessary.

c) Operator starts automated test.

d) Upper and lower peel clamps 20, 22 activate.

e) Peel motion arm 24 performs the peeling test by moving down at the specified test rate.

f) Force data is simultaneously collected with the peel force transducers 40.

g) Upon completion of peeling test, data is displayed and stored.

h) Operator removes specimens 30.

i) All assemblies are moved to initial positions.

j) Test can be repeated at a new temperature.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). In some embodiments, some program code may execute on local computers and some program code may execute on one or more local and/or remote server.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Figure 8:
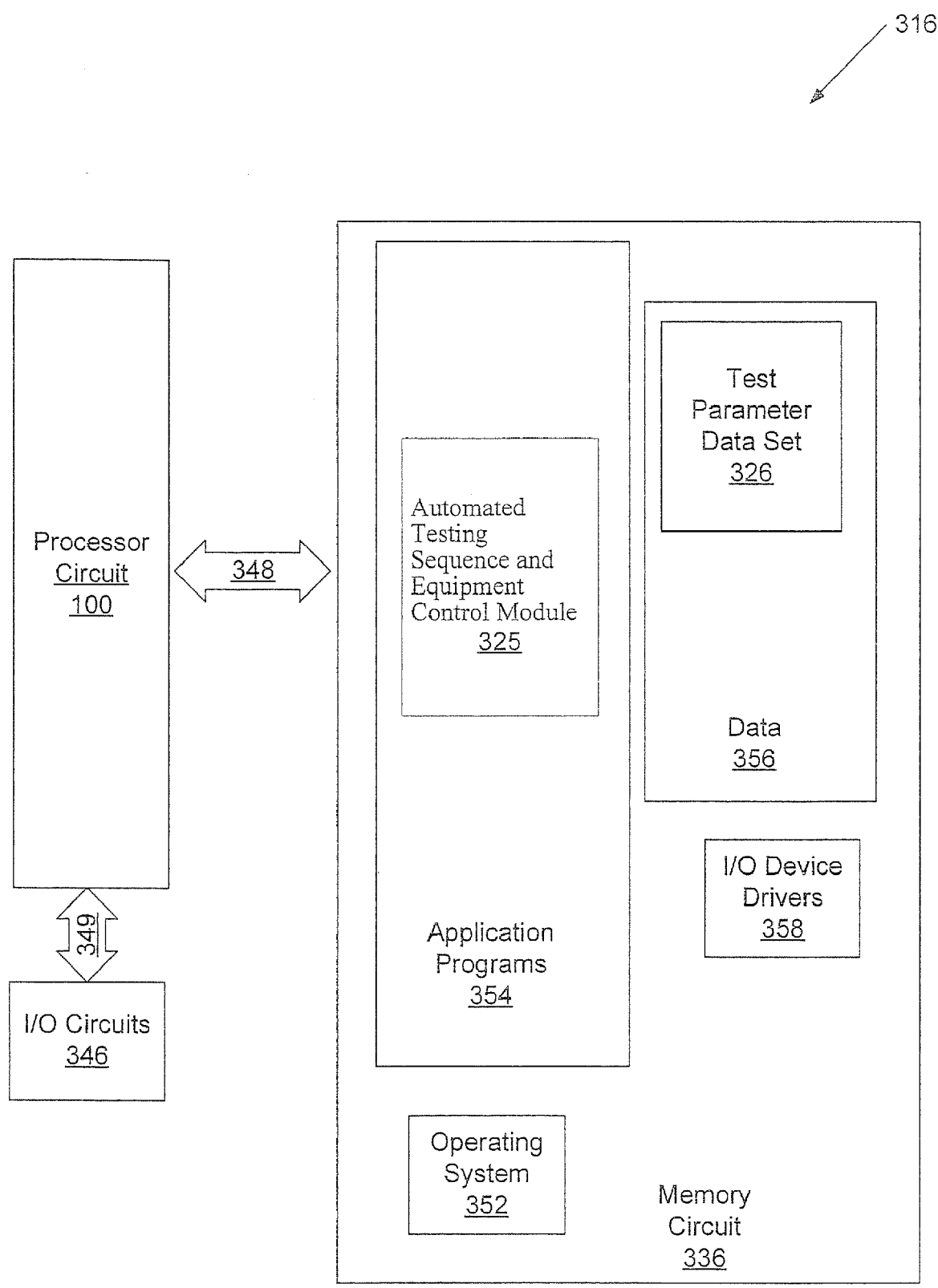
FIG. 8 is a schematic illustration of a data processing system according to embodiments of the present invention.

As illustrated in FIG. 8, embodiments of the invention may be configured as a data processing system 316, which can be used to carry out or direct operations of the rendering, and can include a processor circuit 100, a memory 336 and input/output circuits 346. The data processing system may be incorporated in, for example, one or more of a personal computer, workstation 316, server, router or the like. The system 316 can reside on one machine or between a plurality of machines. The processor 100 communicates with the memory 336 via an address/data bus 348 and communicates with the input/output circuits 346 via an address/data bus 349. The input/output circuits 346 can be used to transfer information between the memory (memory and/or storage media) 336 and another computer system or a network using, for example, an Internet protocol (IP) connection. These components may be conventional components such as those used in many conventional data processing systems, which may be configured to operate as described herein.

In particular, the processor 100 can be commercially available or custom microprocessor, microcontroller, digital signal processor or the like. The memory 336 may include any memory devices and/or storage media containing the software and data used to implement the functionality circuits or modules used in accordance with embodiments of the present invention. The memory 336 can include, but is not limited to, the following types of devices: ROM, PROM, EPROM, EEPROM, flash memory, SRAM, DRAM and magnetic disk. In some embodiments of the present invention, the memory 336 may be a content addressable memory (CAM).

As further illustrated in FIG. 8, the memory (and/or storage media) 336 may include several categories of software and data used in the data processing system: an operating system 352; application programs 354; input/output device drivers 358; and data 356. As will be appreciated by those of skill in the art, the operating system 352 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 358 typically include software routines accessed through the operating system 352 by the application programs 354 to communicate with devices such as the input/output circuits 346 and certain memory 336 components. The application programs 354 are illustrative of the programs that implement the various features of the circuits and modules according to some embodiments of the present invention. Finally, the data 356 represents the static and dynamic data used by the application programs 354 the operating system 352 the input/output device drivers 358 and other software programs that may reside in the memory 336.

The data 356 may include current or historical film test data sets and/or test parameters associated with different testing regimens 326. As further illustrated in FIG. 8, according to some embodiments of the present invention application programs 354 include an Automated Testing Sequence and Equipment Control Module 325. For example, the clamping of the peel clamps can be timed to inflate the clamping member and/or to initiate subsequent testing sequences. The application program 354 may be located in a local server (or processor) and/or database or a remote server (or processor) and/or database, or combinations of local and remote databases and/or servers.

While the present invention is illustrated with reference to the application programs 354 in FIG. 8, as will be appreciated by those of skill in the art, other configurations fall within the scope of the present invention. For example, rather than being application programs 354 these circuits and modules may also be incorporated into the operating system 352 or other such logical division of the data processing system. Furthermore, while the application program 354 is illustrated in a single data processing system, as will be appreciated by those of skill in the art, such functionality may be distributed across one or more data processing systems in, for example, in a client/server arrangement. Thus, the present invention should not be construed as limited to the configurations illustrated in FIG. 8 but may be provided by other arrangements and/or divisions of functions between data processing systems. For example, although FIG. 8 is illustrated as having various circuits and modules, one or more of these circuits or modules may be combined or separated without departing from the scope of the present invention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An automated or semi-automated packaging material testing system, comprising:
   at least one cooperating pair of side-insertion peel clamps for operator loading of film specimens, wherein the side-insertion peel clamps of a respective cooperating pair of side-insertion peel clamps reside vertically aligned, one above another, whereby an operator is able to slidably insert test film from a left or right hand side into both of the side-insertion peel clamps concurrently while the test film is oriented vertically, and wherein the side-insertion peel clamps then automatically grip the test film; and
   at least one peel grip assembly, one for each cooperating pair of side-insertion peel clamps, each respective peel grip assembly including a calibration platform located at an upper portion of the system above and aligned with a corresponding pair of cooperating side-insertion peel clamps, wherein each peel grip assembly also includes a peel force transducer residing below and closely spaced to the calibration platform, and wherein each calibration platform is adapted to releasably hold a calibrated dead weight for periodic calibration of the respective peel force transducer while the respective peel force transducer remains in position in the system.

2. A system according to claim 1, wherein the system includes a plurality of pairs of the side-insertion peel clamps, one for each of a respective different side-by-side test stations, each having the associated peel grip assembly with the corresponding integrated calibration platform, and wherein the respective transducer of each peel grip assembly is attached to an underside of the corresponding calibration platform.

3. A system according to claim 2, wherein each peel grip assembly includes a pair of laterally spaced apart columns which pass freely through openings in a top frame member to attach to the calibration platform, the calibration platform residing above the top frame member, wherein the top frame member extends across the different test stations, whereby a direct, shunt-free load path extends between the peel force transducer and an upper one of the side insertion peel clamps of the corresponding peel clamp pairs.

4. An automated or semi-automated packaging film testing system configured to perform at least one of a hot tack test, a heat seal test and an aged seal test, comprising:
   at least one specimen test station, the at least one test station comprising cooperating upper and lower side-insertion peel clamps configured to allow a film specimen to be slidably inserted therein to releasably hold the film specimen during at least one of an automated: (a) hot tack test, (b) heat seal test and (c) aged seal test, wherein at least one of the upper and lower peel clamps is automatically translatable during the at least one automated test,
   wherein the side-insertion peel clamps reside vertically aligned, one above another, in a specimen loading configuration whereby an operator is able to slidably insert the film specimen from a left or right hand side into both peel clamps concurrently while the film specimen is oriented vertically, and wherein the peel clamps then automatically grip the film specimen to thereby provide fast operating loading of the film specimen,
   wherein the system includes a support platform that includes a top frame attached to a bottom frame by left and right hand frame sides, the support platform residing inside a housing, and wherein the at least one specimen test station comprises at least three test stations residing inside the housing, with the upper and lower side entry peel clamps of each test station residing inside the support platform, the system further comprising a peel grip assembly for each test station in communication with a respective upper side-insertion peel clamp, the peel grip assembly for each test station comprising a transducer for measuring peel force exerted on a specimen as a seal defined by a specimen undergoing evaluation is peeled apart.

5. An automated or semi-automated packaging film testing system configured to perform at least one of a hot tack test, a heat seal test and an aged seal test, comprising:
   at least one specimen test station, the at least one test station comprising cooperating upper and lower side-insertion peel clamps configured to allow a film specimen to be slidably inserted therein to releasably hold the film specimen during at least one of an automated: (a) hot tack test, (b) heat seal test and (c) aged seal test, wherein at least one of the upper and lower peel clamps is automatically translatable during the at least one automated test,
   wherein the side-insertion peel clamps reside vertically aligned, one above another, in a specimen loading configuration whereby an operator is able to slidably insert the film specimen from a left or right hand side into both peel clamps concurrently while the film specimen is oriented vertically, and wherein the peel clamps then automatically grip the film specimen to thereby provide fast operating loading of the film specimen,
   wherein the system is configured to measure peel force using a peel force transducer in communication with the upper peel clamp, the system further comprising an integrated force transducer calibration platform that resides above the peel force transducer and is in communication with the peel force transducer, wherein the integrated force transducer calibration platform is configured to allow calibrated weights to be placed thereon to allow external periodic calibration of the peel force transducer while the peel force transducer remains in position in the device.

6. An automated or semi-automated packaging film testing device configured to perform at least one of a hot tack test, a heat seal test and an aged seal test of a film test specimen, comprising:
   at least one specimen test station, each at least one specimen test station comprising:
   an integrated force transducer calibration platform that resides above a peel force transducer to be in communication with the peel force transducer, wherein the integrated force transducer calibration platform is configured to allow calibrated weights to be placed thereon to allow external calibration of the peel force transducer while the peel force transducer remains in position in the device.

7. A device according to claim 6, wherein the at least one station is a plurality of adjacent stations residing in a common housing, the device further comprising a respective peel grip assembly for each test station, each peel grip assembly comprising an upper peel clamp that releasably engages a test specimen, the upper peel clamps being in communication with a respective peel force transducer.

8. A device according to claim 7, further comprising a controller configured to programmatically direct the test stations to selectively carry out the hot tack test, the heat seal test or the aged seal test, wherein the controller is configured to direct a translating positioning assembly to automatically move to a predetermined aged-seal test start location to accept an aged-seal test specimen, and wherein the positioning assembly aged-seal test start location is different than the start location of the hot tack and heat seal tests.

9. A device according to claim 6, wherein the at least one test station is at least three test stations, and wherein each of the test stations further comprises lower peel clamps that releasably hold a test specimen, a respective one lower clamp for each upper clamp, and wherein, the device is configured to selectively carry out an automated: (a) hot tack test, (b) heat seal test and (c) aged seal test, wherein the lower peel clamps automatically translate in concert during the tests.

10. An automated or semi-automated packaging material testing system, comprising:
 a housing with a top frame, a bottom frame and opposing side frames that define a support platform;
 a plurality of side-by-side testing stations residing within the housing, each testing station attached to the support platform and including:
  a cooperating pair of upper and lower side-insertion peel clamps, wherein the upper and lower peel claims of each peel clamp pair reside vertically aligned, one above another, whereby an operator is able to slidably insert test film from a left or right hand side into both peel clamps while the test film is oriented vertically;
  an upper latch for holding a first end portion of the test film residing above the upper side-insertion peel clamp;
  a lower latch for holding an opposing second end portion of the test film residing below the lower peel clamp; and
  a peel grip assembly including an integral calibration platform residing above the top frame and aligned with a corresponding cooperating peel clamp pair, wherein the peel grip assembly also includes a peel force transducer residing below and closely spaced to the calibration platform, and wherein each platform is adapted to releasably hold a calibrated dead weight for periodic calibration of the respective peel force transducer while the respective peel force transducer remains in position in the system; and
 a controller configured to programmatically direct the test stations to selectively carry out one of a hot tack test, a heat seal test and an aged seal test, wherein the controller is configured to direct at least one of the upper and lower positioning assemblies to automatically move corresponding upper and lower peel clamps of each test station to carry out a selected test.

11. A system according to claim 10, wherein the plurality of test stations is at least three test stations.

12. A system according to claim 10, wherein each peel grip assembly further includes a pair of laterally spaced apart columns that are attached to the upper peel clamp on a lower end and which pass freely through openings in the top frame member at an opposing end to attach to the calibration platform, whereby a direct, shunt-free load path extends between the peel force transducer and an upper one of the side insertion peel clamps of the corresponding peel clamp pairs.

13. A system according to claim 10, wherein the side-insertion peel clamps are configured to allow an operator to slidably insert test film from a left or right hand side into both peel clamps concurrently while the test film is oriented vertically.

14. A system according to claim 10, wherein the plurality of test stations is three.

* * * * *

UNITED STATES PATENT AND TRADEMARK OFFICE
CERTIFICATE OF CORRECTION

PATENT NO. : 7,607,357 B2  
APPLICATION NO. : 11/675165  
DATED : October 27, 2009  
INVENTOR(S) : Stewart et al.

It is certified that error appears in the above-identified patent and that said Letters Patent is hereby corrected as shown below:

In the Claims:

Column 14, Line 60, Claim 6: Correct "external calibration" to read -- periodic calibration --.

Signed and Sealed this

Second Day of February, 2010

David J. Kappos
*Director of the United States Patent and Trademark Office*